(12) United States Patent
Mis et al.

(10) Patent No.: US 9,109,221 B2
(45) Date of Patent: *Aug. 18, 2015

(54) PARTICLES CONTAINING ORGANIC CATALYTIC MATERIALS AND USES

(71) Applicants: Mark R. Mis, Hornell, NY (US);
Mridula Nair, Penfield, NY (US);
Douglas R. Robello, Webster, NY (US)

(72) Inventors: Mark R. Mis, Hornell, NY (US);
Mridula Nair, Penfield, NY (US);
Douglas R. Robello, Webster, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,946

(22) Filed: Nov. 28, 2012

(65) Prior Publication Data

US 2014/0147885 A1    May 29, 2014

(51) Int. Cl.
*C12N 11/04* (2006.01)
*C12N 11/08* (2006.01)
*C12N 11/14* (2006.01)

(52) U.S. Cl.
CPC ............. *C12N 11/04* (2013.01); *C12N 11/08* (2013.01); *C12N 11/14* (2013.01)

(58) Field of Classification Search
CPC ..... A61K 9/1694; A61K 9/2081; A61K 9/50; A61K 47/34; A61K 47/48907; A61K 49/0091; C08G 63/79; C08G 63/81; C08G 63/00; C08G 63/06; C08G 81/00; C08J 9/28; C08J 9/283

See application file for complete search history.

(56) References Cited

U.S. PATENT DOCUMENTS

| | | | |
|---|---|---|---|
| 4,833,060 A | 5/1989 | Nair et al. |
| 4,965,131 A | 10/1990 | Nair et al. |
| 7,754,409 B2 | 7/2010 | Nair et al. |
| 8,110,628 B1 | 2/2012 | Nair et al. |
| 2003/0002029 A1 | 1/2003 | Dukler et al. |
| 2008/0176157 A1 | 7/2008 | Nair et al. |
| 2010/0021838 A1 | 1/2010 | Putnam et al. |
| 2011/0262654 A1 | 10/2011 | Yates et al. |
| 2011/0262858 A1 | 10/2011 | Nair et al. |

FOREIGN PATENT DOCUMENTS

| | | |
|---|---|---|
| WO | 2010/101240 A1 | 9/2010 |
| WO | 2013/016044 A1 | 1/2013 |
| WO | 2013/016080 A2 | 1/2013 |

OTHER PUBLICATIONS

Julio Raba and Horacio A. Mottola, Glucose Oxidase as an Analytical Reagent, 1995, Critical Reviews in Analytical Chemistry, vol. 25(1), pp. 1-42.*

Yi-Yan Yang, Tai-Shung Chung, Ngee Ping Ng, Morphology, drug distribution, and in vitro release profiles of biodegradable polymeric microspheres containing protein fabricated by double-emulsion solvent extraction/evaporation method, 2001, Biomaterials, vol. 22, pp. 231-241.*

Tharwat Tadros, P. lzquierdo, J. Esquena, C. Solans, Formation and stability of nano-emulsions, Advances in Colloid and Interface Science, 2004, vol. 108-109, pp. 303-318.*

Yoon Sung Nam, Jin-Woong Kim Jongwon Shim Sang Hoon Han and Han Kon Kim, Nanosized Emulsions Stabilized by Semisolid Polymer Interphase, 2010, Langmuir, vol. 26(16), pp. 13038-13043.*

Louis R. Nemzer, Austin Schwartz, and A. J. Epstein, Enzyme Entrapment in Reprecipitated Polyaniline Nano- and Microparticles, 2010, Macromolecules, vol. 43, pp. 4324-4330.*

Nemanja Miletic, Aleksandra Nastasovic, Katja Loos, Immobilization of biocatalysts for enzymatic polymerizations: Possibilities, advantages, applications, 2012, Bioresource Technology, vol. 115, pp. 126-135.*

S. M. Kuiper, et al., "Enzymes containing porous polymersomes as nano reaction vessels for cascade reactions", Org. Biomol. Chem., 2008, pp. 4315-4318.

E. E. Gaskell, et al., "Encapsulation and release of alpha-chymotrypsin from poly(glycerol adipate-co-omega-pentadecalactone) microparticles", Research Gate, Journal of Microencapsulation, Jun. 2008.

R. V. Parthasarathy, et al., "enzyme and Chemical Encapsulation in Polymeric Microcapsules", Journal of Applied Polymer Science, vol. 62, (1996) pp. 875-886.

R. M. Crooks, et al., "Dendrimer-Encapsulated Metal Nanoparticles: Synthesis, Characterization, and Applications to Catalysis", Accounts of Chemical Research, vol. 34, No. 3, Mar. 2001, pp. 181-190.

J. Xu, et al., "One-Stage Synthesis of Cagelike Porous Polymeric Microspheres and Application as Catalyst Scaffold of Pd Nanoparticles", Macromolecules 2011, 44, pp. 3730-3738.

A. V. Biradar, et al., "Silica-Dendrimer Core—Shell Microspheres with Encapsulated Ultrasmall Palladium Nanoparticles: Efficient and Easily Recyclable Heterogeneous Nanocatalysts", American Chemical Society, Langmuir 2011, 27, pp. 14408-14418.

L. K. Yeung, et al., "Heck Heterocoupling within a Dendritic Nanoreactor", American Chemical Society, 2001, pp. 14-17.

(Continued)

*Primary Examiner* — Ralph Gitomer
*Assistant Examiner* — Trent Clarke
(74) *Attorney, Agent, or Firm* — J. Lanny Tucker

(57) ABSTRACT

Semi-permeable particle can be used to facilitate chemical reactions such as catalytic reactions. The semi-permeable particles are permeable to molecules having a molar mass of 1000 Daltons or less and have a mode particle size of at least 1 μm. The semi-permeable particles have multiple discrete cavities containing an aqueous solution or suspension of an organic catalytic material. The semi-permeable particles are also impermeable to the organic catalytic materials so they are retained within the multiple discrete cavities, and the semi-permeable particles can be reused multiple times for the same or different chemical reaction.

30 Claims, No Drawings

(56) References Cited

OTHER PUBLICATIONS

T. N. Blanton, et al., "Antibacterial and Antifungal Protection for Toner Image", U.S. Appl. No. 13/235,789, filed Sep. 19, 2011.

M. Nair, et al., "Porous Organic Polymeric Films and Preparation", U.S. Appl. No. 13/686,942, filed Nov. 28, 2012.

M. Nair, et al., "Porous Particles and Methods of Making Them", U.S. Appl. No. 13/686,943, filed Nov. 28, 2012.

D. R. Robello, "Semi-Permeable Particles Having Metallic Catalysts and Uses", U.S. Appl. No. 13/686,941, filed Nov. 28, 2012.

* cited by examiner

PARTICLES CONTAINING ORGANIC CATALYTIC MATERIALS AND USES

COPENDING APPLICATIONS

Reference is made to copending and commonly assigned U.S. Ser. No. 13/686,941 (filed on Nov. 28,2012 by Robello, Nair, Mis, and Dirmyer).

Reference is made to copending and commonly assigned U.S. Ser. No. 13/686,942 (filed on Nov. 28,2012 by Nair and Jones).

Reference is made to copending and commonly assigned U.S. Ser. No. 13/686,943 (filed on Nov. 28,2012 by Nair, Jones, and Mis).

FIELD OF THE INVENTION

The present invention relates to micro-sized semi-permeable particles containing organic catalytic materials such as enzymes. It also relates to various uses of these semi-permeable particles and methods for making them.

BACKGROUND OF THE INVENTION

Porous polymeric particles have been prepared and used for many different purposes. For example, porous particles have been described for use in chromatographic columns, ion exchange and adsorption resins, cosmetic formulations, papers, and paints. The methods for generating pores in polymeric particles are well known in the field of polymer science. However, each particular porous particle often requires unique methods for their manufacture. Some methods of manufacture produce large particles without any ability to control of the pore size while other manufacturing methods control the pore size without controlling the overall particle size.

Marker materials can be included in porous particles so that the particles can be detected for a specific purpose. For example, U.S. Patent Applications 2008/0176157 (Nair et al.) and 2010/0021838 (Putnam et al.) and U.S. Pat. No. 7,754,409 (Nair et al.) describe porous particles and a method for their manufacture, which porous particles are designed to be toner particles for use in electrophotography. Such porous particles typically contain a colorant and can be prepared using a multiple emulsion process in combination with a suspension process (such as "evaporative limited coalescence", ELC) in a reproducible manner and with a narrow particle size distribution.

Still another important use of polymeric particles is as a means for marking documents, clothing, or labels as a "security" tag, for example for authentication of documents using an electrophotographic process and core-shell toner particles containing an infrared emitting component and a detection step. For example, U.S. Patent Application Publication 2003/0002029 (Dukler et al.) describes a method for labeling documents for authentication using a toner particle containing two or more mixed compounds having a characteristic detectable signal.

U.S. Pat. No. 8,110,628 (Nair et al.) describes porous particles and articles containing same that contain various marker materials within discrete pores for specific means of detection. These porous particles can be prepared using multiple water-in-oil emulsions containing the desired markers and pore stabilizing hydrocolloids to prevent coalescence of the pore forming water-in-oil droplets.

Catalytic nanoparticle encapsulation in microcapsules is described by Parthasarathy et al. in *J. Applied Polymer Sci.*, 62, 875-886 (1996). However, these microcapsules are tubular and do not contain multiple discrete cavities.

Organic catalytically reactive materials, such as enzymes, can be used in compositions for many purposes but there is always a need to protect people and the environment from chemicals such as enzymes that are used in chemical reactions. Another desire is to extend the useful lifetime of organic catalytic materials in certain applications by preventing degradation by adventitious hydrolytic enzymes or digestion by microorganisms. There is also desire for improved handling of organic catalytic materials. There is a further desire to find a means for providing micro-sized materials containing nano-sized organic reactive materials that can also be reused while retaining high reactive capability.

SUMMARY OF THE INVENTION

The present invention provides an aqueous slurry of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle has a mode particle size of at least 1 μm, wherein each semi-permeable particle is impermeable to the organic catalytic material, and the semi-permeable particle is permeable to molecules having a molar mass that is 1000 Daltons or less.

This invention also provides a material useful for catalyzing chemical reactions in substantially aqueous media, the material comprising an aqueous slurry of semi-permeable particles of any embodiments of this invention, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, each semi-permeable particle having a mode particle size of at least 1 μm, wherein each semi-permeable particle is impermeable to the organic catalytic material, and each semi-permeable particle is permeable to molecules having a molar mass that is 1000 Daltons or less.

Other embodiments of this invention comprise a method of making an aqueous slurry of a plurality of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable material having a mode particle size of at least 1 μm, wherein each semi-permeable particle is impermeable to the organic catalytic material, and each semi-permeable particle is permeable to molecules having a molar mass that is 1000 Daltons or less, the method comprising:
   providing a first aqueous phase comprising the organic catalytic material and the cavity stabilizing hydrocolloid, both dispersed within the first aqueous phase,
   dispersing the first aqueous phase in an organic solvent comprising the water-insoluble semi-permeable polymer to form a first water-in-oil emulsion,
   dispersing the first water-in-oil emulsion in a second aqueous phase containing a surface stabilizing material to form a water-in-oil-in-water emulsion containing droplets of the water-in-oil emulsion, and
   removing the organic solvent from the droplets to form the aqueous dispersion of a plurality of semi-permeable particles.

In addition, this invention provides a method for causing a chemical reaction, comprising:
   contacting one or more reactive chemicals having a molar mass of 1000 Daltons or less with a slurry of semi-permeable particles,
   each of the semi-permeable particles comprising a water-insoluble semi-permeable polymer providing a continuous polymeric phase including an external particle surface, the semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle has a mode particle size of at least 1 µm,
   wherein each semi-permeable particle is impermeable to the organic catalytic material, and the semi-permeable particle is permeable to molecules of the one or more reactive chemicals having a molar mass of 1000 Daltons or less.

After this chemical reaction, the semi-permeable particles containing the organic catalytic material can be reused one or more times for the same or different chemical reaction.

The present invention provides a number of advantages. The organic catalytic materials used in the present invention can be very expensive and difficult to isolate for recovery and reuse. The relatively large semi-permeable particles in which they are incorporated for this invention allow for their recovery by simple filtration or centrifugation. Little or no organic catalyst material is lost from the semi-permeable particles when the particles are recovered and this provides considerable economic advantages. For example, at least 80% of the organic catalytic material is retained in the semi-permeable particles during storage and on repeated reuse as a catalyst in chemical reactions.

The semi-permeable particles have multiple discreet cavities that allow diffusion of the intended small molecule reactants so that they interact with the organic catalytic material present in at least some of the multiple discrete cavities. This provides desired rapid reaction rates while allowing convenient isolation of the organic catalytic material after use.

Similarly, isolation of the reaction product from the organic catalytic materials is facilitated so that contamination is minimized. In principle, any organic catalytic material can be used in the present invention if it can be solubilized or dispersed in water. Enzymes are specifically contemplated as the organic catalytic materials because they are used in a wide variety of chemical processes in aqueous media, and are usually water-soluble or water-dispersible. Furthermore, as high molar molecules, enzymes will not escape through the walls of the semi-permeable polymeric particles, and can therefore be conveniently isolated and reused in subsequent processes. Thus, the catalytic activity is preserved using the present invention for several reaction cycles in which the organic catalytic materials are retained or encapsulated within at least some of the multiple discrete cavities for a prolonged period after the first use.

The uniform size of the semi-permeable particles of this invention leads to consistent reaction rates and recovery processes. In addition, the semi-permeable particles need not be isolated or dried before they are used. Rather, they are advantageously used in an aqueous slurry.

DETAILED DESCRIPTION OF THE INVENTION

Definitions

As used herein to define various components of solutions, formulations, and components, unless otherwise indicated, the singular forms "a", "an", and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term's definition should be taken from a standard dictionary.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges can be used to achieve substantially the same results as the values within the ranges. In addition, the disclosure of these ranges is intended as a continuous range including every value between the minimum and maximum values.

The terms "semi-permeable particle" and "semi-permeable porous particles" are used herein, unless otherwise indicated, to refer to materials of the present invention, or to materials used in the present invention. They are defined in more detail below.

The term "porogen" refers to a cavity forming agent used to make the semi-permeable particles. In this invention, a porogen can be the aqueous phase of the water-in-oil emulsions (that is the first aqueous phase), the cavity stabilizing hydrocolloid, or any other additive in the aqueous phase that can modulate the porosity of the semi-permeable particles.

In this invention, the term "discrete cavity" is used instead of "pore" to define a void within the continuous polymeric phase of the semi-permeable particles. Discrete cavities can be interconnected to form a network of voids or they can exist in isolation from other discrete cavities.

The semi-permeable particles can include "micro", "meso", and "macro" discrete cavities, which according to the International Union of Pure and Applied Chemistry, are the classifications recommended for discrete cavities less than 2 nm, from 2 nm to 50 nm, and greater than 50 nm, respectively. The semi-permeable particles can include closed multiple discrete cavities of all sizes and shapes (discrete cavities entirely within the continuous polymeric phase). While there may be open cavities on the surface of the semi-permeable particle, such open cavities are not desirable and are generally present only by accident. The size of the semi-permeable particle, the formulation, and manufacturing conditions are the primary controlling factors for discrete cavity size.

The multiple discrete cavities can have an average size of at least 200 nm and up to and including 5 µm or typically at least 500 nm and up to and including 3 µm. For spherical discrete cavities, this average size is an "average diameter". For non-spherical discrete cavities, the average size refers to the average largest dimension". The multiple discrete cavities can have the same or different average sizes. Discrete cavity size can be determined by analyzing Scanning Electron Microscopy (SEM) images of fractured semi-permeable particles using a commercial statistical analysis software package. For example, the "average" discrete cavity size can be determined by calculating the average diameter of 20 measured discrete cavities.

Uses

The semi-permeable particles of this invention can have various uses including but not limited to use in drug delivery devices, cosmetic formulations, fuel cells, pharmaceuticals and diagnostic and analytical devices, and chemical reactors used for organic syntheses or other chemical processes, food processing, laundering, waste water treatment, air pollution, bio fuels refining, or in applications where an organic catalytic material is needed for a chemical reaction.

Semi-Permeable Particles

The semi-permeable particles comprise a continuous polymeric phase formed from one or more water-insoluble semi-permeable polymers (defined below) including an external particle surface and multiple discrete cavities dispersed within the continuous polymeric phase and an aqueous solution or suspension of one or more organic catalytic materials (defined below) that are exclusively within at least some of the multiple discrete cavities.

In most embodiments, the continuous polymeric phase of the semi-permeable particles has the same composition. That is, the continuous polymeric phase is uniform in composition including any additives that may be incorporated into the water-insoluble semi-permeable polymer. In addition, if mixtures of water-insoluble semi-permeable polymers are used in the continuous polymeric phase, those mixtures are dispersed uniformly throughout.

The semi-permeable particles are generally prepared, as described below, using multiple water-in-oil emulsions in combination with an aqueous suspension process, such as in the ELC process. The water-in-oil emulsion can be originally prepared and used to provide multiple discrete cavities (and the contained organic catalytic materials) in the semi-permeable particles.

The water-insoluble semi-permeable polymers useful in the practice of this invention to provide the continuous polymeric phase can be any type of polymer or resin that is capable of being dissolved in a suitable solvent (described below) and is insoluble in water. In addition, these water-insoluble polymers are "semi-permeable", meaning that relatively large organic catalytic materials (for example, having an average diameter greater than 1 nm) are unable to penetrate the continuous polymeric phase that makes up the walls of the multiple discrete cavities (and are therefore retained indefinitely) while smaller reactants and products can freely diffuse through the discrete cavity walls and the continuous polymeric phase.

Useful water-insoluble semi-permeable polymers include but are not limited to, those derived from vinyl monomers such as styrene monomers and condensation monomers such as esters and mixtures thereof. Such polymers include but are not limited to, homopolymers and copolymers such as polyesters, styrenic polymers (for example polystyrene and polychlorostyrene), mono-olefin polymers (for example, polymers formed from one or more of ethylene, propylene, butylene, and isoprene), vinyl ester polymers (for example, polymer formed from one or more of vinyl acetate, vinyl propionate, vinyl benzoate, and vinyl butyrate), acrylic polymers for example formed from one or more α-methylene aliphatic mono-carboxylic acid esters (for example, polymers formed from one or more of methyl acrylate, ethyl acrylate, butyl acrylate, dodecyl acrylate, octyl acrylate, phenyl acrylate, methyl methacrylate, ethyl methacrylate, butyl methacrylate, and dodecyl methacrylate), vinyl ether polymers (such as polymers formed from one or more of vinyl methyl ether, vinyl ethyl ether, and vinyl butyl ether), vinyl ketone polymers (for example, polymers formed from one or more of vinyl methyl ketone, vinyl hexyl ketone, and vinyl isopropenyl ketone), and aliphatic cellulose ester polymers. Particularly useful water-insoluble, semi-permeable polymers include polystyrenes (including homopolymers and copolymers of styrene derivatives), polyesters, styrene/alkyl acrylate copolymers, styrene/alkyl methacrylate copolymers, styrene/acrylonitrile copolymers, styrene/butadiene copolymers, styrene/maleic anhydride copolymers, polyethylene resins, and polypropylene resins. Other useful water-insoluble semi-permeable polymers include polyurethanes, urethane acrylic copolymers, epoxy resins, silicone resins, polyamide resins, modified rosins, paraffins, and waxes. Still other useful water-insoluble semi-permeable polymers are polyesters of aromatic or aliphatic dicarboxylic acids with one or more aliphatic diols, such as polyesters of isophthalic or terephthalic or fumaric acid with diols such as ethylene glycol, cyclohexane dimethanol, and bisphenol adducts of ethylene or propylene oxides. The polyesters can be saturated or unsaturated.

Particularly useful water-insoluble, semi-permeable polymers are selected from polyesters, polyamides, polyurethanes, styrenic polymers, mono-olefin polymers, vinyl ester polymers, acrylic polymers, vinyl ether polymers, vinyl ketone polymers, and aliphatic cellulose ester polymers.

One or more cavity stabilizing hydrocolloids are disposed within at least some of the multiple discrete cavities, and typically, these compounds are disposed within essentially all (at least 95%) of the multiple discrete cavities. Suitable cavity stabilizing hydrocolloids include but are not limited to, both naturally occurring and synthetic, water-soluble or water-swellable polymers selected from the group consisting of cellulose derivatives [such as for example, carboxymethyl cellulose (CMC) that is also referred to as sodium carboxymethyl cellulose], gelatin (for example, alkali-treated gelatin such as cattle bone or hide gelatin, or acid treated gelatin such as pigskin gelatin), gelatin derivatives (for example, acetylated gelatin and phthalated gelatin), proteins and protein derivatives, hydrophilic synthetic polymers [such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, and methacrylamide copolymers], water soluble microgels, polyelectrolytes [such as a polystyrene sulfonate, poly(2-acrylamido-2-methylpropanesulfonate), and a polyphosphate], and mixtures of any of these classes of materials.

In order to stabilize the initial water-in-oil emulsions so that they can be held without ripening or coalescence, it is desired that the cavity stabilizing hydrocolloids in the aqueous phase have a higher osmotic pressure than that of the first oil phase depending on the solubility of water in the oil. This reduces the diffusion of water into the oil phases from the aqueous phases and thus the ripening caused by migration of water between the water droplets. One can achieve a higher osmotic pressure in the aqueous phase either by increasing the concentration of the cavity stabilizing hydrocolloid or by increasing the charge on the cavity stabilizing hydrocolloid (the counter-ions of the dissociated charges on the cavity stabilizing hydrocolloid increase its osmotic pressure). It can be advantageous to have weak base or weak acid moieties in the cavity stabilizing hydrocolloids that allow for their osmotic pressures to be controlled by changing the pH. Such cavity stabilizing hydrocolloids are considered "weakly dissociating hydrocolloids". For these weakly dissociating hydrocolloids, the osmotic pressure can be increased by buffering the pH to favor dissociation, or by simply adding a base (or acid) to change the pH of the aqueous phase to favor dissociation. One example of such a weakly dissociating hydrocolloid is CMC that has a pH sensitive dissociation (the carboxylate is a weak acid moiety). For CMC, the osmotic pressure can be increased by buffering the pH, for example using a pH 6-8 buffer, or by simply adding a base to raise the pH of the aqueous phase to favor dissociation. For aqueous phases containing CMC the osmotic pressure increases rapidly as the pH is increased from 4-8.

Other synthetic polyelectrolyte hydrocolloids such as polystyrene sulfonate (PSS), poly(2-acrylamido-2-methyl-propanesulfonate) (PAMS), and polyphosphates are also useful cavity stabilizing hydrocolloids.

Particularly useful cavity stabilizing hydrocolloids are selected from the group consisting of carboxymethyl cellulose (CMC), a gelatin, a protein or protein derivative, a hydrophilic synthetic polymer, a water-soluble microgel, a polystyrene sulfonate, poly(2-acrylamido-2-methylpropanesulfonate), and a polyphosphate.

The cavity stabilizing hydrocolloids are soluble in water and have no negative impact on multiple emulsification processes, and have no negative impact on the organic catalytic materials. The cavity stabilizing compounds can be optionally crosslinked to minimize migration of cavity stabilizing hydrocolloids from the multiple discrete cavities.

The amount of the one or more cavity stabilizing hydrocolloids in the semi-permeable particles will depend on the amount of porosity and size of the multiple discrete cavities desired and the molecular weight and charge of the cavity stabilizing hydrocolloid that is chosen. For example, the one or more cavity stabilizing hydrocolloids can be present in the semi-permeable particles in an amount of at least 0.5 weight % and up to and including 20 weight %, or typically at least 1 weight % and up to and including 10 weight %, based on total semi-permeable particle dry weight.

To provide additional stability of multiple discrete cavities in the water-in-oil emulsions and resulting semi-permeable particles, the oil phase can also comprise low HLB polymeric emulsifiers preferably, one or more amphiphilic (low HLB) block copolymers (emulsifiers) that are disposed at the interface of the multiple discrete cavities and the continuous polymeric solid phase of the semi-permeable particles. The term "amphiphilic" is generally used to refer to a molecule having a polar, water-soluble group that is attached to a non-polar, water-insoluble hydrocarbon or oleophilic group. "HLB" refers to the well known term "hydrophilic-lipophilic balance" and refers to the measure of the degree to which a compound is hydrophilic or lipophilic and is determined for a given polymer or molecule using the known Griffin's mathematical method where HLB equals 20 ($M_h/M$) wherein $M_h$ equals the molecular weight of the hydrophilic block in the molecule and M equals the molecular weight of the whole block copolymer. Thus, the amphiphilic block copolymers useful in the present invention have a low HLB value, meaning that they are more lipophilic than hydrophilic, and they comprise both water-soluble blocks (hydrophilic) and water-insoluble blocks (lipophilic), and the HLB value is less than or equal to 6.

The molecular weights of the water-soluble component and the oleophilic components are not critical as long as the resulting amphiphilic block copolymer has an HLB equal to or less than 6. For example, the block copolymers can have a hydrophilic block having a molecular weight ($M_h$) of at least 100 and up to and including 25,000, and a hydrophobic (or oleophilic) block having a molecule weight ($M_n$) of at least 500 to and including 100,000.

In some embodiments, the amphiphilic block copolymer comprises a hydrophilic segment comprising polyethyleneoxide and a hydrophobic (oleophilic) segment comprising polycaprolactone. Further details of such block copolymers are provided in Kowalski et al., Macromol. Rapid Commun., 1998, Vol. 19, 567, and in U.S. Pat. No. 5,429,826 (Nair et al.) that is incorporated herein by reference.

Other useful hydrophilic components for amphiphilic block copolymers can be derived from poly(2-ethyloxazolines), poly(saccharides), and dextrans.

The oleophilic block component of the amphiphilic block copolymers useful in the present invention can also be selected from many common components, including but not limited to, oleophilic components derived from monomers such as: styrene, caprolactone, propiolactone, β-butyrolactone, δ-valerolactone, ε-caprolactam, lactic acid, glycolic acid, hydroxybutyric acid, and derivatives of lysine and glutamic acid. Particularly useful oleophilic components of the amphiphilic block copolymers useful in this invention are derived from polymers such as certain polyesters, polycarbonates, and polyamides, or more particularly polyesters such as poly(caprolactone) and its derivatives, poly(lactic acid), poly(3-hydroxybutyrate-co-3-hydroxyvalerate), poly(3-hydroxybutyrate), and poly(glycolic acid).

A particularly useful amphiphilic block copolymer can be defined as an A-B block copolymer that comprises a hydrophilic block (A) comprising polyethyleneoxide and a hydrophobic (oleophilic) block (B) comprising polycaprolactone represented herein as PEO-b-PCL.

The amphiphilic block copolymers can also be represented as "A-B-A" type wherein A and B are defined above. Although this invention is directed mainly towards amphiphilic block copolymers, graft copolymers and random graft copolymers containing similar components are also useful.

The amphiphilic block copolymer can be present in the resulting semi-permeable particles in an amount of at least 1 weight % and up to and including 99.5 weight %, or at least 2 weight % and up to and including 50 weight %, based on total semi-permeable particle weight. It is contemplated that in some embodiments, the amphiphilic block copolymer can comprise the continuous polymeric solid phase of the semi-permeable particles and at the same time, function as the low HLB material that is disposed at the interface of the multiple discrete cavities.

In the method of this invention, the amphiphilic block copolymer can be present in the oil phase in an amount of at least 0.2 weight % and up to and including 30 weight %, or typically of at least 0.5 weight % and up to and including 15 weight %, based on the total oil phase weight.

While low HLB amphiphilic block copolymers are preferred as the optional emulsifiers for preparing the water-in-oil emulsions, other polymeric emulsifiers are also envisioned as useful depending on the composition of the oil phase. An example of such an emulsifier is GRINDSTED® PGPR 90, polyglycerol polyricinolate emulsifier, obtained from Dupont.

The semi-permeable particles used in this invention are permeable to molecules having a molar mass of 1000 Daltons or less (1000 or less molecular weight, or 1000 g or less per mole of the molecule). In this context, the term "permeable"

refers to the ability of a molecule to penetrate the continuous polymeric phase that composes the walls of the multiple discrete cavities at a useful rate. Such molecules to which the semi-permeable particles are permeable include but are not limited to, organic molecules that are partially or completely soluble in water.

The semi-permeable particles of this invention generally have a mode particle size of at least 1 µm and up to and including 100 µm, or typically of at least 4 µm and up to an including 50 µm. This mode particle size can be measured by automated image analysis and flow cytometry using any suitable equipment designed for that purpose. The mode particle size represents the most frequently occurring diameter for spherical semi-permeable particles and the largest diameter for the non-spherical semi-permeable particles.

In general, the volume of the multiple discrete cavities in the semi-permeable particles is at least 10% and up to and including 60%, or more likely at least 20% and up to and including 50% based on the total dry semi-permeable particle volume. This porosity can be measured by the mercury intrusion technique.

The semi-permeable particles can be spherical or non-spherical depending upon the desired use. The shape of semi-permeable particles can be characterized by an "aspect ratio" that is defined as the ratio of the largest perpendicular length to the longest length of the semi-permeable particle. These lengths can be determined for example by optical measurements using a commercial particle shape analyzer such as the Sysmex FPIA-3000 (Malvern Instruments). For example, semi-permeable particles that are considered "spherical" for this invention can have an aspect ratio of at least 0.95 and up to and including 1. For the non-spherical semi-permeable particles of this invention, the aspect ratio can be at least 0.4 and up to and including 0.95.

The semi-permeable particles comprise one or more types of organic catalytic materials that are disposed within at least some of the multiple discrete cavities, and usually within nearly all of the multiple discrete cavities. These organic catalytic materials can include but are not limited to, high molar mass organocatalysts such as those described by Lipshutz and Ghorai, *Organic Letters* 2012, 14, pp. 422-425), and enzymes, and generally have a molecular weight of at least 1000 Daltons and up to and including $10^7$ Daltons. For example useful enzymes are selected from the group consisting of catalase, peroxidase, superoxide dismutase, hydrolase, carbonic anhydrase, cytochrome P450, alcohol dehydrogenase, aspartate aminotransferase, luciferase, glucose oxidase, glucose isomerase, trypsin, papain (papaya proteinase I), protease, lipase, esterase, urease, cellulase, amylase, lactase, phytase, amidase, thermolysin, diacetyl reductase, and nitrile hydrolase.

In some embodiments, the water-insoluble semi-permeable polymer and the aqueous solution or dispersion of the organic catalytic material are present in the semi-permeable particles at a weight ratio of at least 0.04 to and including 3.5, or typically at a weight ratio of at least 0.06 to and including 2.

The semi-permeable particles can also comprise one or more surface stabilizing materials on the external particle surface of each particle. Useful surface stabilizing materials include but are not limited to, stabilizer polymers such as poly(vinyl pyrrolidone) and poly(vinyl alcohol), inorganic stabilizers such as clay particles, colloidal or fumed silica (for example LUDOX™ or NALCO™), or polymer latex particles as described in modified ELC process described in U.S. Pat. No. 4,833,060 (Nair et al.), U.S. Pat. No. 4,965,131 (Nair et al.), U.S. Pat. No. 2,934,530 (Ballast et al.), U.S. Pat. No. 3,615,972 (Morehouse et al.), U.S. Pat. No. 2,932,629 (Wiley), and U.S. Pat. No. 4,314,932 (Wakimoto et al.), the disclosures of which are hereby incorporated by reference. Any combinations of these surface stabilizing materials can also be used.

The actual amount of surface stabilizing material present on the semi-permeable particles depends on the size of the semi-permeable particles desired, which in turn depends upon the volume and weight ratios of the various phases used for making the emulsions (described below). While not intending to be limiting for this invention, the amount of surface stabilizing material on the semi-permeable particles can be at least 0.5 weight % and up to and including 30 weight %, or typically at least 2 weight % and up to and including 20 weight %, based on the total dry weight of the semi-permeable particles and depending upon the particle size of the surface stabilizing material (for example, colloidal or fumed silica particles).

In some embodiments of the aqueous slurries of semi-permeable particles, each semi-permeable particle comprises a solution or dispersion of the organic catalytic material in at least some of the multiple discrete cavities, the organic catalytic material being selected from the group consisting of high molar mass organocatalysts such as that described by Lipshutz and Ghorai (noted above), and enzymes such as catalase, peroxidase, superoxide dismutase, hydrolase, carbonic anhydrase, cytochrome P450, alcohol dehydrogenase, aspartate aminotransferase, luciferase, glucose oxidase, glucose isomerase, trypsin, papain, protease, lipase, esterase, urease, cellulase, amylase, lactase, phytase, amidase, thermolysin, diacetyl reductase, and nitrile hydrolase, and each semi-permeable particle has an equivalent spherical diameter (ESD) of at least 2 µm and up to and including 40 µm.

Methods of Preparation

A process for making the semi-permeable particles involves basically a multi-step process. A first aqueous phase (primarily water as a solvent) is formed having dispersed therein molecules of the organic catalytic materials and dissolved therein one or more cavity stabilizing hydrocolloids (both described above). The organic catalytic materials can be present in this first aqueous phase in amount of at least 1 ppm and up to and including 10,000 ppm. The one or more cavity stabilizing hydrocolloids can be present in this first aqueous phase in an amount of at least 0.5 weight % and up to and including 20 weight %, or typically of at least 1 weight % and up to and including 10 weight %, all based on the total first aqueous phase weight.

This first aqueous phase is then dispersed in a suitable organic solution (one or more organic solvents described below) or oil phase comprising one or more of the water-insoluble semi-permeable polymers (described above) that eventually form a continuous semi-permeable polymeric phase, to form a first emulsion (first water-in-oil emulsion). These water-insoluble polymers are dissolved in the organic solvent. The first aqueous phase creates the multiple discrete cavities in the resulting semi-permeable particles. Ways to form the first emulsion are described below.

Salts can be added to the first aqueous phase to buffer the emulsion and optionally to control the osmotic pressure of the aqueous phases. When CMC is used as a cavity stabilizing hydrocolloid, for example, the osmotic pressure can be increased by using inorganic salts or a buffer. The first emulsion can also contain additional cavity forming agents such as ammonium carbonate.

The semi-permeable particles can be prepared and provided in dry powder form or as an aqueous slurry. They can be used in either form. However, an aqueous slurry of the semi-permeable particles is a particularly useful.

Any suitable organic solvent that will dissolve the water-insoluble, semi-permeable polymer(s) and that is also immiscible with water can be used to prepare the organic solvent used in the first emulsion. Such organic solvents include but are not limited to, ethyl acetate, propyl acetate, chloromethane, dichloromethane, vinyl chloride, trichloromethane, carbon tetrachloride, ethylene chloride, trichloroethane, toluene, xylene, cyclohexanone, 2-nitropropane, dimethyl carbonate, and mixtures of two or more of these solvents. Ethyl acetate and propyl acetate are generally good solvents for many useful water-insoluble semi-permeable polymers while being sparingly soluble in water, and they are readily removed as described below by evaporation.

Optionally, the organic solution is a mixture of two or more water-immiscible solvents chosen from the list given above. For example, the organic solution can comprise a mixture of one or more of the above organic solvents with a water-immiscible non-solvent for the water-insoluble semi-permeable polymer such as heptane, cyclohexane, and diethylether that is added in a proportion that is insufficient to precipitate the water-insoluble semi-permeable polymer prior to drying and isolation.

Depending upon the ultimate use of the semi-permeable particles, the first emulsion can also include various additives, generally that are added to the water-insoluble semi-permeable polymer prior to its dissolution in the organic solvent, during dissolution, or after the dissolution step itself. Such additives can include but are not limited to, colorants, charge control agents, shape control agents, compatibilizers, wetting agents, surfactants, plasticizers, and release agents such as waxes and lubricants, that are not within the cavities. Combinations of these materials can also be used. The first or second aqueous phase can also include a buffering salt examples of which are readily known in the art.

The next step in the formation of porous particles according to this invention involves forming a water-in-oil-in-water emulsion by dispersing the first emulsion (first water-in-oil emulsion) in a second aqueous phase containing a surface stabilizing material to form a second emulsion (water-in-oil-in-water emulsion) that contains droplets of the first water-in-oil emulsion. The surface stabilizing materials can be either stabilizer polymers such as poly(vinyl pyrrolidone) or poly(vinyl alcohol) or more likely a colloidal silica such as that available as LUDOX® or NALCO® silica or latex particles in a modified ELC process such as described in U.S. Pat. No. 4,965,131 (Nair et al.), U.S. Pat. No. 2,934,530 (Ballast et al.), U.S. Pat. No. 3,615,972 (Cohrs et al.), U.S. Pat. No. 2,932,629 (Wiley), and U.S. Pat. No. 4,314,932 (Wakimoto et al.), all of which are incorporated herein by reference.

The second aqueous phase comprises primarily water as the solvent, and it can also comprise buffering salts, shape control agents, surface stabilizing materials, and co-stabilizers or promoters to drive the surface stabilizing materials, particularly colloidal material, to the interface of the water-in-oil droplets in the second aqueous phase.

Suitable co-stabilizers or promoters include sulfonated polystyrenes, alginates, derivatives of cellulose, tetramethyl ammonium hydroxide or chloride, triethylphenyl ammonium hydroxide, triethylphenyl ammonium hydroxide, triethylphenyl ammonium chloride, diethylaminoethylmethacrylate, water-soluble complex resinous amine condensation products, such as the water soluble condensation product of diethanol amine and adipic acid, such as poly(adipic acid-co-methylaminoethanol), water soluble condensation products of ethylene oxide, urea, and formaldehyde and polyethylene-imine; gelatin, glue, casein, albumin, gluten, and the like. A particularly useful promoter is poly(adipic acid-co-methylaminoethanol). The amount of any of the co-stabilizers or promoters used in the present invention can be at least 0.1 weight % to and including 20 weight % based on the total dry weight of the surface stabilizing materials.

The first emulsions used to prepare the semi-permeable particles of this invention can be prepared by any known emulsifying technique and conditions using any type of mixing and shearing equipment. Such equipment includes but is not limited to, a batch mixer, planetary mixer, single or multiple screw extruder, dynamic or static mixer, colloid mill, high pressure homogenizer, sonicator, or a combination thereof. While any high shear type agitation device is useful, a particularly useful homogenizing device is the Microfluidizer® such as Model No. 110T produced by Microfluidics Manufacturing operating at >5000 psi. In this device, the droplets of the first aqueous phase can be dispersed and reduced in size in the organic solution in a high flow agitation zone and, upon exiting this zone, the size of the droplets in the dispersed aqueous phase is reduced to uniform sized dispersed droplets in the organic solution. The temperature of the process can be modified to achieve the optimum viscosity for emulsification of the droplets and to minimize evaporation of the organic solution.

Specifically, the water-in-oil emulsion is mixed with the second aqueous phase containing a surface stabilizing material such as colloidal silica and an optional co-stabilizer, to form an aqueous suspension of droplets of the water-in-oil emulsion in the second aqueous phase, which is then subjected to shear or extensional mixing or shear flow processes, such as through an orifice device to reduce the droplet size of the suspension, yet greater than the particle size of the first water-in-oil emulsion, to achieve narrow size distribution droplets through the limited coalescence process. The pH of the second aqueous phase is generally between 4 and 7 when silica particles are used as the surface stabilizing material. Useful surface stabilizing materials and co-stabilizers or promoters are described above. Colloidal or fused silica (for example LUDOX™ or NALCO™) is particularly useful. The actual amount of surface stabilizing material used depends upon the final desired size of the porous particles, which in turn depends upon the volume and weight ratios of the various phases used for making the multiple emulsions. While not intending to be limiting for this invention, the amount of surface stabilizing material in the second emulsion can be at least 0.1 weight % and up to and including 10 weight %, or typically at least 0.2 weight % and up to and including 7 weight %, based on the total weight of the water-in-oil phase in the water-in-oil-in-water emulsion and depending upon the particle size of the surface stabilizing material.

When the second (water-in-oil-in-water) emulsion is formed, shear or extensional mixing or flow process is controlled in order to minimize disruption of the distinct droplets of the first aqueous phase in the organic solution. Droplet size reduction is achieved by homogenizing the second emulsion through a capillary orifice device, or other suitable flow geometry. The shear field used to create the droplets can be created using standard shear geometries, such as an orifice plate or capillary. However, the flow field can also be generated using alternative geometries, such as packed beds of beads, or stacks or screens that impart an additional extensional component to the flow. It is well known in the literature that membrane-based emulsifiers can be used to generate multiple emulsions. The techniques allow the droplet size to be tailored across a wider range of sizes by adjusting the cavity volume or mesh size, and can be applied across a wide range of flow rates. The back pressure suitable for producing acceptable particle size and size distribution is at least 100 psi (689.5 kilonewtons/m$^2$) and up to and including 5000 psi (34,475 kilonewtons/m$^2$), or typically at least 500 psi (3447.5 kilonewtons/m$^2$) and up to and including 3000 psi (20,685 kilonewtons/m$^2$). The flow rate is generally at least 1000 ml/min and up to and including 6000 ml/min, particularly when a capillary orifice device is used.

The final size of the semi-permeable particles and the final size of the multiple discrete cavities of the semi-permeable particles can be impacted by the osmotic mismatch between the osmotic pressure of the first and second aqueous phases. At each interface, the larger the osmotic pressure gradient present, the faster the diffusion rate where water will diffuse from the lower osmotic pressure phase to the higher osmotic pressure phase depending on the solubility and diffusion coefficient in the organic solution.

The organic solution is removed after the first emulsion droplets are formed in the second aqueous phase. Removal of the organic solvents provides precursor semi-permeable particles that can be subjected to isolation from the second aqueous phase, washing, and optionally drying techniques to provide the desired semi-permeable particles. The details of these procedures depend upon the water solubility and boiling points of the organic solvents in the organic solution relative to the temperature of the solvent removal process. Generally, organic solvents can be removed by evaporation using removal apparatus such as a rotary evaporator or a flash evaporator. The semi-permeable particles can then be isolated after removing the organic solvents by filtration or centrifugation, washing to remove any contamination from the second aqueous phase, optionally followed by drying, for example, in an oven at 40° C. that also removes any water remaining in the multiple discrete cavities. Advantageously, the semi-permeable particles can be used directly without removing the water in the multiple discrete cavities, which is as an aqueous slurry in water. Optionally, the semi-permeable particles can be treated with alkali to remove any surface stabilizing material if desired.

Optionally, after the second emulsion has been formed, additional water can be added to the second emulsion (water-in-oil-in-water emulsion) to increase the size of the multiple discrete cavities by creating an osmotic pressure mismatch between the first and second aqueous phases allowing for the migration of water from the second aqueous phase to the first.

Thus, in this method of preparation, the organic catalytic material can be selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase.

In addition, in such semi-permeable particles, the water-insoluble semi-permeable polymer and aqueous solution or suspension of the organic catalytic material can be present at a weight ratio of at least 0.04 to and including 3.5.

Alternatively, in the method for preparing the semi-permeable particles, the organic solution described above can be replaced with one or more ethylenically unsaturated polymerizable monomers (generally in liquid form) and a polymerization initiator to form a second emulsion (water-in-oil-in-water emulsion). Thus, the organic solution comprises predominantly the ethylenically unsaturated polymerizable monomers as the organic solvents. The ethylenically unsaturated polymerizable monomers in the second emulsion can be polymerized for example through the application of heat or radiation (such as actinic or IR radiation) after the second emulsion is formed and before any organic solvents are removed to form one or more suitable water-insoluble semi-permeable polymers. Any organic solvents can be present in such small amounts and have sufficient solubility in water that it can be removed by washing with water. This washing can occur simultaneously with a filtration process. The resulting suspension of polymerized precursor semi-permeable particles can be isolated and re-slurried in water as described earlier to yield desired semi-permeable particles useful in this invention.

In addition, if desired, the water-immiscible ethylenically unsaturated polymerizable monomer(s) can contain one or more water-insoluble, semi-permeable polymers as described above. Useful ethylenically unsaturated polymerizable monomers and polymerization initiators would be readily apparent to one skilled in the art in order to achieve the desired continuous polymeric phase.

The shape of the semi-permeable particles can be modified if necessary by reducing the spherical nature (sphericity) of the particles (for example, an aspect ratio of less than 0.95, or an aspect ratio of from 0.4 and up to and including 0.95). In the method used to prepare the semi-permeable particles, additives (shape control agents) can be incorporated into the first aqueous phase or in the organic solution to modify the shape, aspect ratio, or morphology of the resulting semi-permeable particles. The shape control agents can be added after or prior to forming the second emulsion. Some useful shape control agents are quaternary ammonium tetraphenylborate salts described in U.S. Patent Application Publication 2007/0298346 (Ezenyilimba et al.), metal salts described in U.S. Patent Application Publication 2008/0145780 (Yang et al.), carnauba waxes described in U.S. Pat. No. 5,283,151 (Santilli), SOLSPERSE® hyperdispersants as described in U.S. Pat. No. 5,968,702 (Ezenyilimba et al.), metal salts as described in U.S. Pat. No. 7,655,375 (Yang et al.), and zinc organic complexes as described in U.S. Pat. No. 7,662,535 (Yang et al.). All of these publications are incorporated herein by reference. The more desirable shape control agents are polyethyloxazoline, fatty acid modified polyesters such as EFKA® 6225 and EFKA® 6220 from Ciba BASF, and phosphate esters of alkoxylated phenols such as SynFac® 8337.

The method for causing a chemical reaction according to this invention can be carried out by contacting a reactive chemical having a molar mass of 1000 Daltons or less with a slurry of semi-permeable particles of this invention. This contact can be achieved by stirring or otherwise agitating a slurry of the organic catalytic material-containing semi-permeable particles with a substantially aqueous solution of a suspension of the organic catalytic material in a vessel for the required period of time, maintaining the temperature of the mixture as desired by any conventional means such as a thermostated jacket around the vessel. In a second embodiment, a column can be packed with the organic catalytic material-containing semi-permeable particles, and a substantially aqueous solution of a suspension of the organic catalytic material can be allowed to flow through the stationary "bed" of semi-permeable particles to affect the desired chemical reaction. The temperature of the column can be maintained by conventional means to achieve a desired reaction rate. During these reactive procedures, the amount of organic catalytic materials remaining (retained) in the semi-permeable particles is at least 80 weight % of the original amount (weight) of organic catalytic materials that were incorporated into the semi-permeable particles during manufacture. In many embodiments, the amount of retained organic catalytic materials is at least 90 weight % of the original amounts (weight).

This retention of the organic catalytic materials is particularly useful so the semi-permeable particles can be used more than once. Thus, a slurry of semi-permeable particles can be reused multiple times for the same or different catalytic reaction. For example, after the first chemical reaction using the organic catalytic material, the slurry of semi-permeable particles can reused one or more times by contacting the semi-permeable particles with the same or different chemical reactant under suitable conditions.

The present invention provides at least the following embodiments and combinations thereof, but other combinations of features are considered to be within the present invention as a skilled artisan would appreciate from the teaching of this disclosure:

1. An aqueous slurry of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle has a mode particle size of at least 1 μm, wherein each semi-permeable particle is impermeable to the organic catalytic material, and the semi-permeable particle is permeable to molecules having a molar mass that is 1000 Daltons or less.

2. The aqueous slurry of semi-permeable particles of embodiment 1, wherein the organic catalytic material is an enzyme.

3. The aqueous slurry of semi-permeable particles of embodiment 1 or 2, wherein the organic catalytic material is selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase.

4. The aqueous slurry of semi-permeable particles of any of embodiments 1 to 3, wherein the water-insoluble semi-permeable polymer and the aqueous solution or dispersion of the organic catalytic material are present in each semi-permeable particle at a weight ratio of at least 0.04 to and including 3.5.

5. The aqueous slurry of semi-permeable particles of any of embodiments 1 to 4, wherein the water-insoluble semi-permeable polymer is selected from a polyester, polyamide, polyurethane, styrenic polymer, mono-olefin polymer, vinyl ester polymer, and acrylic polymer, vinyl ether polymer, vinyl ketone polymer, and aliphatic cellulose ester polymer.

6. The aqueous slurry of semi-permeable particles of any of embodiments 1 to 5, wherein the cavity stabilizing hydrocolloid is selected from the group consisting of carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropanesulfonate), and a polyphosphate.

7. The aqueous slurry of semi-permeable particles of any of embodiments 1 to 6, wherein each semi-permeable particle further comprises an amphiphilic (low HLB) block copolymer that is disposed at the interface of the multiple discrete cavities and the continuous polymeric phase.

8. The aqueous slurry of semi-permeable particles of any of embodiments 1 to 7, wherein each semi-permeable particle has a mode particle size of at least 1 μm and up to and including 100 μm.

9. The aqueous slurry of semi-permeable particles of any of embodiments 1 to 8, wherein the volume of the cavities in each semi-permeable particle is at least 10% and up to and including 60% of the total semi-permeable particle volume.

10. The aqueous slurry of semi-permeable particles of any of embodiments 1 to 9, wherein the average discrete cavity size is at least 200 nm to and including 5 μm.

11. The aqueous slurry of semi-permeable particles of any of embodiments 1 to 10 wherein each semi-permeable particle further comprises a surface stabilizing material on the external particle surface.

12. The aqueous slurry of semi-permeable particles of any of embodiments 1 to 11, wherein each semi-permeable particle further comprises colloidal or fumed silica on the external particle surface.

13. The aqueous slurry of semi-permeable particles of any of embodiments 1 to 12, wherein each semi-permeable particle comprises a solution or dispersion of the organic catalytic material in at least some of the discrete cavities, the organic catalytic material being selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase, and each semi-permeable particle has a mode particle size of at least 2 μm and up to and including 40 μm.

14. A material useful for catalyzing chemical reactions in substantially aqueous media, the material comprising an aqueous slurry of semi-permeable particles of any of embodiments 1 to 13.

15. A method of making an aqueous slurry of a plurality of semi-permeable particles of any of embodiments 1 to 13, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable material having a mode particle size of at least 1 μm, wherein each semi-permeable particle is impermeable to the organic catalytic material, and each semi-permeable particle is permeable to molecules having a molar mass that is 1000 Daltons or less, the method comprising:

providing a first aqueous phase comprising the organic catalytic material and the cavity stabilizing hydrocolloid, both dispersed within the first aqueous phase, dispersing the first aqueous phase in an organic solvent comprising the water-insoluble semi-permeable polymer to form a first water-in-oil emulsion, dispersing the first water-in-oil emulsion in a second aqueous phase containing a surface stabilizing material to form a water-in-oil-in-water emulsion containing droplets of the water-in-oil emulsion, and removing the organic solvent from the droplets to form the aqueous dispersion of a plurality of semi-permeable particles.

16. The method of embodiment 15, wherein the water-insoluble semi-permeable polymer in the semi-permeable particles is selected from a polyester, polyamide, polyurethane, styrenic polymer, mono-olefin polymer, vinyl ester polymer, and acrylic polymer, vinyl ether polymer, vinyl ketone polymer, and aliphatic cellulose ester polymer.

17. The method of embodiment 15 or 16, wherein the cavity stabilizing hydrocolloid is selected from the group consisting of carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropanesulfonate), and a polyphosphate.

18. The method of any of embodiments 15 to 17, wherein each of the plurality of semi-permeable particles further comprises a surface stabilizing material on the external particle surface.

19. The method of any of embodiments 15 to 18, wherein the organic catalytic material is an enzyme.

20. The method of any of embodiments 15 to 19, wherein the organic catalytic material is selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase.

21. The method of any of embodiments 15 to 20, wherein the water-insoluble semi-permeable polymer and aqueous solution or suspension of the organic catalytic material are present at a weight ratio of at least 0.04 to and including 3.5.

22. The method of any of embodiments 15 to 21, wherein the water-insoluble semi-permeable polymer is selected from a polyester, polyamide, polyurethane, styrenic polymer, mono-olefin polymer, vinyl ester polymer, and acrylic polymer, vinyl ether polymer, vinyl ketone polymer, and aliphatic cellulose ester polymer.

23. A method for causing a chemical reaction, comprising:
contacting a reactive chemical having a molar mass of 1000 Daltons or less with the slurry of semi-permeable particles of any of embodiments 1 to 13,
wherein each semi-permeable particle is impermeable to the organic catalytic material, and the semi-permeable particle is permeable to molecules of the reactive chemical having a molar mass of 1000 Daltons or less.

24. The method of embodiment 23, wherein at least 80% of the organic catalytic material is retained in the semi-permeable particles after storage for more than 30 days at room temperature as an aqueous slurry.

25. The method of any of embodiments 23 or 24, wherein after chemical reaction of the organic catalytic material with the reactive chemical, the slurry of semi-permeable particles is reused by contacting the semi-permeable particles with the same or different chemical reactant.

The following Examples are provided to illustrate the practice of this invention and are not meant to be limiting in any manner.

The carboxy methyl cellulose, sodium salt solution and the polycaprolactone used in the examples below were obtained from Sigma-Aldrich.

The amphiphilic block copolymer of polyethylene oxide and polycaprolactone (PEO-b-PCL) was prepared using the procedure described in U.S. Pat. No. 5,429,826 (Nair et al.) and was designed to have following molecular weights in the block components where the first number is the molecular weight of the hydrophilic block segment and the second number is the molecular weight of the oleophilic block segment: 5,000-25,000.

The poly(dl-lactic acid) was obtained from Polysciences Inc.

The Kao E (a bisphenol polyester resin) was obtained from Kao Specialties Americas LLC a part of Kao Corporation (Japan).

Polycaprolactone (MW 45,000) can be obtained from Sigma Aldrich Company.

Piccotoner® 1221 a styrene-butyl acrylate copolymer was obtained from Hercules-Sanyo, Inc. (Wilmington, Del.).

Grinsted® PGPR 90, a poly(glycerol)-poly(ricinoleate) emulsifier was obtained from Danisco USA Inc.

The poly(methylamino ethanol adipate) (AMAE) co-stabilizer was prepared using known procedures and starting materials.

Glucose oxidase and papain were obtained from Sigma-Aldrich. Catalase and horseradish peroxidase were obtained from Worthington Biochemical Corporation.

The Nalco® 1060 colloidal silica was obtained from Nalco Company as a 50 weight % dispersion.

The particle size of the semi-permeable particles according to the present invention size was characterized using optical microscopy and using a Sysmex FPIA-3000 automated particle size analyzer from Malvern Instruments.

Invention Example 1

Preparation of Slurry of Semi-Permeable Particles Using Polycaprolactone and Glucose Oxidase In this example the weight ratio of the water-insoluble semi-permeable polymer to the aqueous solution of the organic catalytic material is 0.26. A first water phase (W1) was prepared using 40.3 g of a 3 weight % solution of a carboxy methyl cellulose, sodium salt solution (250,000) in water along with 21.4 g of a 0.015 weight % glucose oxidase solution in 50 mmolar (pH 6.0) phosphate buffer. The oil phase (O) was prepared using 36.5 g of a 35.5 weight % solution of poly(caprolactone) in ethyl acetate, 12.1 g of a 23.5 weight % solution of poly(ethylene oxide-co-b-caprolactone) in ethyl acetate and 153.0 g of ethyl acetate. To this oil phase was added the W1 phase followed by mixing using a Silverson L4R Mixer fitted with a small holed disintegrating head. The resulting water-in-oil (W1/O) emulsion was further homogenized by using a Microfluidizer model 110T from Microfluidics at a pressure of 8000 psi. This water-in-oil emulsion was added to a second water phase (W2) comprising 13.7 g of a 50 weight % solution of Nalco® 1060 colloidal silica in water, 419.8 g of a 207 mmolar pH 4 citrate/phosphate buffer, and 6.9 g of a 10 weight % solution of poly (methyl amino ethanol) adipate (co-stabilizer) in water.

The resulting mixture was stirred using a Silverson L4R Mixer fitted with a large holed disintegrating head. The ethyl acetate was evaporated from the mixture using a Buchi ROTA VAPOR RE120 evaporator at 40° C. under reduced pressure to yield semi-permeable particles containing glucose oxidase in the resulting discrete cavities. The resulting semi-permeable particles were washed on a glass frit funnel, and stored as a suspension (slurry) in 50 mmolar pH 6.0 phosphate buffer. The amount of protein encapsulated within the resulting 3-8 µm semi-permeable particles was found to be 91 µg/g (dry basis), as determined by assay of the W2 aqueous phase (the typical procedure is described below in Invention Example 27).

Invention Example 2

Preparation of Slurry of Semi-Permeable Particles Using Polycaprolactone and Glucose Oxidase In this example the weight ratio of the water-insoluble semi-permeable polymer to the aqueous solution of the organic catalytic material is 0.51. The procedure of Invention Example 1 was followed except that 21.4 g of a 0.015 weight % glucose oxidase solution in 50 mmolar (pH 6.0) phosphate buffer was used in W1 aqueous phase. The oil phase was made using 81.1 g of a 35.5 weight % solution of polycaprolactone in ethyl acetate, 12.1 g of a 23.5 weight % solution of poly(ethylene oxide-co-b-caprolactone) in ethyl acetate, and 108.4 g of ethyl acetate. The amount of enzyme encapsulated in the resulting 3-8 micron semi-permeable particles was found to be 95 μg/g (dry basis), as determined by assay of the W2 aqueous phase (typical procedure described below in Invention example 27).

Invention Example 3

Preparation of Slurry of Semi-Permeable Particles Using Polycaprolactone and Glucose Oxidase In this example the weight ratio of the water-insoluble semi-permeable polymer to the aqueous solution of the organic catalytic material is 0.64. The procedure of Invention Example 1 was followed except that 21.4 g of a 0.019 weight % glucose oxidase solution in 50 mmolar (pH 6.0) phosphate buffer was used in W1 aqueous phase. The oil phase was made using 103.4 g of a 35.5 weight % solution of poly (caprolactone) in ethyl acetate, 12.1 g of a 23.5 weight % solution of poly(ethylene oxide-co-b-caprolactone) in ethyl acetate, and 86.1 g of ethyl acetate. The amount of enzyme encapsulated in the resulting 3-8 μm semi-permeable particles was found to be 96 μg/g (dry basis), as determined by assay of the W2 aqueous phase (typical procedure described below in Invention Example 27).

Invention Example 4

Preparation of Slurry of Semi-Permeable Particles Using Polycaprolactone and Glucose Oxidase In this example the weight ratio of the water-insoluble semi-permeable polymer to the aqueous solution of the organic catalytic material is 0.39. The semi-permeable particles of this invention were formulated to have a narrower size distribution than in Examples 1-3. The procedure of Invention Example 1 was followed except that 21.4 g of a 0.011 weight % glucose oxidase solution in 50 mmolar (pH 6.0) phosphate buffer was used in the W1 aqueous phase. The oil phase was made using 85.3 g of a 23.6 weight % solution of poly(caprolactone) in ethyl acetate, 17.1 g of a 23.7 weight % solution of poly(ethylene oxide-co-b-caprolactone) in ethyl acetate, and 98.9 g of ethyl acetate. After mixing with large holed disintegrating head the slurry was run through an orifice homogenizer to narrow the particle size distribution. The amount of enzyme encapsulated in the resulting 3-6 μm semi-permeable particles was found to be 91 μg/g (dry basis), as determined by assay of the W2 aqueous phase (typical procedure described below in Invention Example 27).

Invention Example 5

Preparation of Slurry of Semi-Permeable Particles Using Polycaprolactone and Papain The procedure of Invention Example 1 was followed except that 21.4 g of a 1.0 weight % papain solution in water was used in the W1 aqueous phase. The amount of enzyme encapsulated in the resulting 3-8 μm semi-permeable particles was found to be 5600 μg/g (dry basis), as determined by assay of the W2 aqueous phase (typical procedure described below in Invention Example 27).

Invention Example 6

Preparation of Slurry of Semi-Permeable Particles Using Polycaprolactone and Horseradish Peroxidase The procedure of Invention Example 1 was followed except that 21.4 g of a 0.04 weight % horseradish peroxidase solution in 50 mmolar (pH 7.0) phosphate buffer was used in the W1 aqueous phase. The amount of enzyme encapsulated in the resulting 3-8 μm semi-permeable particles was found to be 199 μg/g (dry basis), as determined by assay of the W2 aqueous phase (typical procedure described below in Invention Example 27).

Invention Example 7

Preparation of Slurry of Semi-Permeable Particles Using Bisphenol Polyester and Glucose Oxidase The procedure of Invention Example 1 was followed except that 21.4 g of a 0.005 weight % glucose oxidase solution in 50 mmolar (pH 6.0) phosphate buffer was used in the W1 aqueous phase. The oil phase was made using 37.1 g of a 27.2 weight % solution of Kao E polyester in ethyl acetate. No stabilizer was added to oil phase. No co-stabilizer was added to the W2 aqueous phase. The amount of enzyme encapsulated in the resulting 6-10 μm semi-permeable particles was found to be 95 μg/g (dry basis), as determined by assay of the W2 aqueous phase (typical procedure described below in Invention Example 27).

Invention Example 8

Preparation of Slurry of Semi-Permeable Particles using Styrene-Butyl Acrylate Copolymer and Glucose Oxidase The procedure of Invention Example 1 was followed except that 21.4 g of a 0.012 weight % glucose oxidase solution in 50 mmolar (pH 6.0) phosphate buffer was used in the W1 aqueous phase. The oil phase was made using 86.4 g of a 26.3 weight % solution of Piccotoner® 1221 in ethyl acetate, 1.63 g of PGPR 90® as stabilizer, and 114.4 g of ethyl acetate. No co-stabilizer was added to the W2 aqueous phase. The amount of enzyme encapsulated in the resulting 6-10 μm semi-permeable particles was found to be 88 μg/g (dry basis), as determined by assay of the W2 aqueous phase (typical procedure described below in Invention Example 27).

Invention Example 9

Preparation of Slurry of Semi-Permeable Particles Using Poly(dl-Lactic Acid) Polymer and Glucose Oxidase The procedure of Invention Example 1 was followed except that 21.4 g of a 0.012 weight % glucose oxidase solution in 50 mmolar (pH 6.0) phosphate buffer was used in the W1 aqueous phase. The oil phase (O) was prepared using 82.1 g of a 26.0 weight % solution of poly(dl-lactic acid) in ethyl acetate, 12.1 g of a 23.5 weight % solution of poly (ethylene oxide-co-β-caprolactone) in ethyl acetate, and 107.0 g of ethyl acetate. No co-stabilizer was put into the W2 aqueous phase. The amount of enzyme encapsulated in the resulting 3-8 µm semi-permeable particles was found to be 80 µg/g (dry basis), as determined by assay of the W2 aqueous phase (typical procedure described below in Invention Example 27).

Invention Example 10

Preparation of Slurry of Semi-Permeable Particles Using Bisphenol Polyester and Papain The procedure of Invention Example 1 was followed except that 21.4 g of a 1.0 weight % papain solution in water was used in the W1 aqueous phase. The oil phase (O) was made using 80.4 g of a 20.1 weight % solution of Kao E in ethyl acetate and 121.2 g of ethyl acetate. No stabilizer was added to oil phase. No co-stabilizer was added to the W2 aqueous phase. The amount of enzyme encapsulated in the resulting 6-10 µm semi-permeable particles was found to be 5600 µg/g (dry basis), as determined by assay of the W2 aqueous phase (typical procedure described below in Invention Example 27).

Invention Example 11

Preparation of Slurry of Semi-Permeable Particles Using Polycaprolactone and Catalase The procedure of Invention Example 1 was followed except 15.5 g of a 3 weight % solution of a carboxy methyl cellulose, sodium salt solution in water along with 49.3 g of a 0.004 weight % catalase solution in water was used in the W1 aqueous phase. The oil phase was made using 29.7 g of a 25.6 weight % solution of poly(caprolactone) in ethyl acetate, 11.9 g of a 24.8 weight % solution of poly(ethylene oxide-co-b-caprolactone) in ethyl acetate, and 157.3 g of ethyl acetate. The second aqueous phase (W2) was made using 4.3 g of a 50 weight % solution of Nalco® 1060 colloidal silica in water, 433.8 g of a pH 5.4 50 mmolar citrate/phosphate buffer, and 2.2 g of a 10 weight % solution of poly(methyl amino ethanol) adipate (co-stabilizer) in water. The amount of enzyme encapsulated in the resulting 3-8 µm semi-permeable particles was found to be 200 µg/g (dry basis), as determined by assay of the W2 aqueous phase (typical procedure described below in Invention Example 27).

Invention Example 12

Preparation of Slurry of Semi-Permeable Particles Using Bisphenol Polyester and Catalase The procedure of Invention Example 1 was followed except 20.0 g of a 3 weight % solution of carboxy methyl cellulose, sodium salt solution in water along with 44.8 g of a 0.002 weight % catalase solution in water was used in the W1 aqueous phase. The oil phase was made using 32.2 g of a 28.1 weight % solution of Kao E in ethyl acetate, and 166.8 g of ethyl acetate. No stabilizer was put into oil phase. The second aqueous phase (W2) was made using 4.3 g of a 50 weight % solution of Nalco® 1060 colloidal silica in water, 435.6 g of a pH 5.4 50 mmolar citrate/phosphate buffer. No co-stabilizer was used in the W2 aqueous phase. The amount of enzyme encapsulated in the resulting 6-10 µm semi-permeable particles was not determined by assay of the W2 aqueous phase. Instead 100% encapsulation was assumed.

Invention Example 13

Assay of Slurry of Semi-Permeable Particles of Invention Example 1) Polycaprolactone and Glucose Oxidase)

A typical procedure for assaying the activity of glucose oxidase in the semi-permeable particles of his invention was performed by following the peroxidation (catalyzed by horseradish peroxidase) of o-dianisidine with hydrogen peroxide which is formed during the oxidation of glucose catalyzed by glucose oxidase contained in the semi-permeable particles. To a clean vial, were added 3 ml of a 0.008 weight % solution of o-dianisidine in 100 mmolar pH 6.0 phosphate buffer, and 0.6 ml of an 18 weight % solution of glucose. To a clean cuvette, were added 1.5 ml of the noted o-dianisidine solution and 0.1 ml of a 200 µg/ml solution of horseradish peroxidase. Upon temperature equilibration, 0.2 ml of aqueous slurry of an aqueous slurry of semi-permeable particles as prepared in Invention Example 1 was added to the vial with stirring. After a period of time, the dispersion in the vial was filtered through a 0.45 µm nylon filter and 1.9 ml of the filtrate was transferred to the cuvette and the absorbance of this solution was recorded at 460 nm corresponding to the oxidation products of o-dianisidine. This experiment was repeated for different lengths of time and the measured increase in absorbance over time is proportional to the activity in units/mg of glucose oxidase contained in the semi-permeable particles as shown below.

| Time (minutes) | $A_{460\,nm}$ |
| --- | --- |
| 0 | 0 |
| 5.0 | 0.08 |
| 10.0 | 0.19 |

These data show that the semi-permeable particles of this invention showed catalytic activity. The activity of the glucose oxidase encapsulated within the semi-permeable particles was calculated to be 31 U/mgP (Units per mg of protein or enzyme).

Invention Example 14

Assay of Slurry of Semi-Permeable Particles of Invention Example 2 (Polycaprolactone and Glucose Oxidase)

The procedure of Invention Example 13 was followed except an aqueous slurry of semi-permeable particles as prepared in Invention Example 2 was used.

| Time (minutes) | $A_{460\,nm}$ |
| --- | --- |
| 0 | 0 |
| 5.0 | 0.04 |
| 10.0 | 0.10 |

These data show that the semi-particles of this invention also showed catalytic activity. The activity of the glucose oxidase encapsulated within the semi-permeable particles was calculated to be 15 U/mgP.

Invention Example 15

Assay of Slurry of Semi-Permeable Particles of Invention Example 3 (Polycaprolactone and Glucose Oxidase)

The procedure of Invention Example 13 was followed except an aqueous slurry of semi-permeable particles of this invention as prepared in Invention Example 3 was used.

| Time (minutes) | $A_{460\,nm}$ |
| --- | --- |
| 0 | 0 |
| 5.0 | 0.01 |
| 10.0 | 0.03 |

These data show that the semi-permeable particles of this invention showed catalytic activity. The activity of the glucose oxidase encapsulated within the semi-permeable particles was calculated to be 5 U/mgP.

The data from Invention Examples 13, 14, and 15 show that when the weight ratio of the water-insoluble semi-permeable polymer to organic catalytic material was decreased, the catalytic activity increased.

Invention Example 16

Assay of Slurry of Semi-Permeable Particles of Invention Example 4 (Polycaprolactone and Glucose Oxidase)

The procedure of Invention Example 13 was followed except an aqueous slurry of semi-permeable particles as prepared in Invention Example 4 was used.

| Time (minutes) | $A_{460\,nm}$ |
| --- | --- |
| 0 | 0 |
| 5.0 | 0.26 |
| 10.0 | 0.38 |
| 22.0 | 0.76 |

These data show that the semi-permeable particles of this invention showed catalytic activity. The activity of the glucose oxidase encapsulated within the semi-permeable particles was calculated to be 19.6 U/mgP.

Invention Example 17

Assay of Slurry of Semi-Permeable Particles of Invention Example 5 (Polycaprolactone and Papain)

A typical procedure for assaying the activity of papain in the semi-permeable particles of this invention was performed by following the papain catalyzed hydrolysis of sodium benzoyl-L-arginine ethyl ester. The acid produced during the reaction was titrated against the 1M sodium hydroxide. To a clean vessel were added 4.0 ml of a 50 mmolar solution of L-cysteine in 20 mmolar ethylenediaminetetraacetic acid (pH was adjusted to 6.2 with 1 molar sodium hydroxide), 4.0 ml of a 3 molar sodium chloride solution, and 28 ml of an 80 mmolar solution of sodium benzoyl-L-arginine ethyl ester. The resulting solution was equilibrated to 25° C. in a water bath. Once equilibrated, 4.0 ml of an aqueous slurry of semi-permeable particles of the present invention containing papain as prepared in Invention Example 5 was added. When the pH had fallen to 6.20, 50 µl of a 20 mmolar NaOH titrate solution was added. This was considered as time zero. When the pH again dropped to 6.20, an additional 50 µl of the 20 mmolar NaOH solution was added and the time was recorded. This procedure was repeated 5 to 6 times. The amount of NaOH titrate used over time is proportional to the activity in units/mg of papain

| Time (minutes) | Volume NaOH (ml) |
| --- | --- |
| 5.00 | 0.05 |
| 8.75 | 0.10 |
| 12.63 | 0.15 |
| 16.92 | 0.20 |
| 20.88 | 0.25 |
| 24.95 | 0.30 |

These data show that the amount of NaOH needed to keep the pH at 6.2 increased over time which indicates catalytic activity. The activity of the enzyme encapsulated within the semi-permeable particles was calculated to be 0.52 U/mgP.

Invention Example 18

Assay of Slurry of Semi-Permeable Particles of Invention Example 6 (Polycaprolactone and Horseradish Peroxidase)

A typical procedure for assaying the activity of horseradish peroxidase in the semi-permeable particles of this invention was performed by following the oxidation of 4-aminoantipyridine with hydrogen peroxide catalyzed by horseradish peroxidase. To a clean vessel were added 7.0 ml of a solution of 0.0025 molar 4-aminoantipyrine and 0.17 molar phenol. To this solution was added 7.5 ml of a 0.0017 molar solution of hydrogen peroxide. Upon temperature equilibration, 0.5 ml of an aqueous slurry of semi-permeable particles of this invention containing horseradish peroxidase as prepared in Invention Example 6 was added to the vial with stirring. After a given length of time, the dispersion was filtered through a 0.45 µm nylon filter and the absorbance was recorded at 510 nm. The increase in absorbance was recorded at 510 nm for a given time. The experiment was repeated for different times and the increase in absorbance over time is proportional to the activity in units/mg of horseradish peroxidase.

| Time (minutes) | $A_{510\,nm}$ |
| --- | --- |
| 0 | 0 |
| 5.0 | 0.006 |
| 15.0 | 0.024 |
| 30.0 | 0.064 |

These data show that the semi-permeable particles of this invention showed catalytic activity. The activity of the horseradish peroxidase encapsulated within the semi-permeable particles was calculated to be 4.4 U/mgP.

Invention Example 19

Assay of Slurry of Semi-Permeable Particles of Invention Example 7 (Bisphenol Polyester and Glucose Oxidase)

The procedure of Invention Example 13 was followed except an aqueous slurry of semi-permeable particles of this invention as prepared in Invention Example 7 was used.

| Time (minutes) | $A_{460\,nm}$ |
| --- | --- |
| 0 | 0 |
| 5.0 | 0.12 |
| 10.0 | 0.24 |
| 22.0 | 0.55 |

These data show that the semi-permeable particles of this invention showed catalytic activity. The activity of the glucose oxidase encapsulated within the semi-permeable particles was calculated to be 14.2 U/mgP.

Invention Example 20

Assay of Slurry of Semi-Permeable Particles of Invention Example 8 (Styrene-Butyl Acrylate Copolymer and Glucose Oxidase)

The procedure of Invention Example 13 was followed except an aqueous slurry of semi-permeable particles of the present invention as prepared in Invention Example 8 was used.

| time (minutes) | $A_{460\,nm}$ |
| --- | --- |
| 0.0 | 0.00 |
| 5.0 | 0.02 |
| 10.0 | 0.04 |
| 15.0 | 0.07 |

These data show that the semi-permeable particles of this invention showed catalytic activity. The activity of the glucose oxidase encapsulated within the semi-permeable particles was calculated to be 5.5 U/mgP.

Invention Example 21

Assay of Slurry of Semi-Permeable Particles of Invention Example 9 (Poly(dl-Lactic Acid) Polymer and Glucose Oxidase)

The procedure of Invention Example 13 was followed except an aqueous slurry of semi-permeable particles of the present invention as prepared in Invention Example 9 was used.

| Time (minutes) | $A_{460\,nm}$ |
| --- | --- |
| 0 | 0 |
| 5.0 | 0.12 |
| 10.0 | 0.24 |
| 15.0 | 0.32 |

These data show that the semi-permeable particles of this invention showed catalytic activity. The activity of the glucose oxidase encapsulated within the semi-permeable particles was calculated to be 14.5 U/mgP.

Invention Example 22

Assay of Slurry of Semi-Permeable Particles of Invention Example 10 (Bisphenol Polyester and Papain)

The procedure of Invention Example 17 was followed except an aqueous slurry of semi-permeable particles of the present invention as prepared in Invention Example 10 was used.

| Time (minutes) | Volume NaOH(ml) |
| --- | --- |
| 5.00 | 0.05 |
| 8.56 | 0.10 |
| 12.23 | 0.15 |
| 15.35 | 0.20 |
| 18.76 | 0.25 |
| 22.10 | 0.30 |

These data show that the amount of NaOH needed to keep the pH at 6.2 increased over time which indicates catalytic activity. The activity of the papain encapsulated within the semi-permeable particles was calculated to be 0.60 U/mgP.

Invention Example 23

Assay of Slurry of Semi-Permeable Particles of Invention Example 11 (Polycaprolactone and Catalase)

A typical procedure for assaying the activity of catalase contained in the semi-permeable particles of this invention was performed by following the degradation of hydrogen peroxide catalyzed by catalase. To a clean vessel were added 38.0 ml of Reagent grade water and 20.0 ml of a 0.059 molar solution of hydrogen peroxide. Upon temperature equilibration, 2.0 ml of an aqueous slurry of semi-permeable particles of this invention containing catalase, as prepared in Invention Example 11 was added to the vessel with stirring. After a given length of time, the dispersion in the vessel was filtered through a 0.45 μm nylon filter and the absorbance was recorded at 240 nm as noted above. This procedure was repeated for different lengths of time and the change in absorbance over time is proportional to the activity of catalase in units/mg of catalase.

| Time (minutes) | $A_{240\,nm}$ |
| --- | --- |
| 0 | 0.81 |
| 30.0 | 0.74 |
| 90.0 | 0.65 |

These data show that the semi-permeable particles of this invention showed catalytic activity. The activity of the catalase encapsulated within the semi-permeable particles was calculated to be 107 U/mgP.

Invention Example 24

Assay of Slurry of Semi-Permeable Particles of Invention Example 12 (Bisphenol Polyester and Catalase)

This assay was performed as in Invention Example 23. To a clean cuvette was added 1.9 ml of Reagent grade water and 1.0 ml of a 0.059 molar solution of hydrogen peroxide. Upon temperature equilibration with stirring, 0.1 ml of an aqueous slurry of semi-permeable particles of the present invention containing catalase, as prepared in Invention Example 12 was added. The change in absorbance over time is proportional to the activity of catalase in units/mg of catalase (U/mgP).

| Time (minutes) | $A_{240\,nm}$ |
| --- | --- |
| 0.50 | 1.10 |
| 0.67 | 1.10 |
| 0.83 | 1.10 |

-continued

| Time (minutes) | $A_{240\,nm}$ |
|---|---|
| 1.00 | 1.08 |
| 1.17 | 1.07 |
| 1.33 | 1.07 |
| 1.50 | 1.06 |
| 1.67 | 1.06 |
| 1.83 | 1.05 |
| 2.00 | 1.05 |

These data show that the semi-permeable particles of this invention exhibited catalytic. The activity of the catalase encapsulated within the semi-permeable particles was calculated to be 6393 U/mgP.

Invention Example 25

Reuse of Slurry of Semi-Permeable Particles of Invention Example 4 (Polycaprolactone and Glucose Oxidase)

To a clean vial, were added 255 ml of a 0.008 weight % solution of o-dianisidine in 100 mmolar pH 6.0 phosphate buffer, and 51 ml of an 18 weight % solution of glucose. To a clean cuvette, were added 1.5 ml of the noted o-dianisidine solution and 0.1 ml of a 200 µg/ml solution of horseradish peroxidase. Upon temperature equilibration, 17 ml of an aqueous slurry of semi-permeable particles of the present invention as prepared in Invention Example 4 was added to the vial with stirring. At a given length of time, the dispersion in the vial was filtered through a 0.45 µm nylon filter and 1.9 ml of the filtrate was transferred to the cuvette and the absorbance of this solution was recorded at 460 nm. Upon completion of the assay, the semi-permeable particles were isolated on a glass frit funnel, washed several times with water, and suspended in a 50 mmolar pH 6.0 phosphate buffer. This procedure was repeated until a total of 5 assays were performed on the isolated and washed semi-permeable particles.

| Assay | Activity (U/mgP) |
|---|---|
| 1 | 14.0 |
| 2 | 13.2 |
| 3 | 13.8 |
| 4 | 12.0 |
| 5 | 12.2 |

These data show that the semi-permeable particles of this invention can be reused by washing and isolating with negligible loss in catalytic activity.

Invention Example 26

Storage Activity of Slurry of Semi-Permeable Particles of Invention Example 4 (Polycaprolactone and Glucose Oxidase)

Storage activity is defined as the activity of slurry of semi-permeable particles with encapsulated organic catalytic material (for example, an enzyme) stored at specified conditions greater than 24 hours. The procedure of Invention Example 13 was followed except an aqueous slurry of semi-permeable particles of the present invention as prepared in Invention Example 4 was used. The slurry was stored at 4° C. in between assays.

| Storage Time (days) | Activity (U/mgP) |
|---|---|
| 1 | 14.0 |
| 18 | 15.9 |
| 70 | 16.4 |

These data show that there is no loss of catalytic activity after storage of the slurry of semi-permeable particles of this invention over the indicated time.

Invention Example 27

Encapsulation Efficiency of a Slurry of Semi-permeable Particles of Invention Example 1 (Polycaprolactone and Glucose Oxidase)

Encapsulation efficiency is defined as the percentage of total organic catalytic material (for example, an enzyme) that is successfully encapsulated in the semi-permeable particles after completion of the particle-making process.

To a clean cuvette were added 2.5 ml of a 0.008 weight % solution of o-dianisidine in 100 mmolar pH 6.0 phosphate buffer, 0.3 ml of an 18 weight % solution of glucose, and 0.1 ml of a 200 µg/ml solution of horseradish peroxidase. Upon temperature equilibration, 0.1 ml of the W2 aqueous phase of an aqueous slurry of semi-permeable particles of this invention as prepared in Invention Example 1 was added to the cuvette. The increase in absorbance was recorded at 460 nm over time. This increase in absorbance over time was compared to the increase in absorbance of the assay of the free organic catalytic material (enzyme, as described in Comparative Example 6 below) to determine the amount of organic catalytic material in the W2 aqueous phase. Since the amount of organic catalytic material is known in the free organic catalytic material assay, the amount of organic catalytic material is easily calculated for the W2 aqueous phase. Based on the amount of organic catalytic material in the W2 aqueous phase the encapsulation efficiency was calculated to be 90.8%.

Invention Example 28

Encapsulation Efficiency of Slurry of Semi-permeable Particles of Invention Example 2 (Polycaprolactone and Glucose Oxidase)

The procedure of Invention Example 27 was followed except the W2 aqueous phase of an aqueous slurry of semi-permeable particles of the present invention as prepared in Inventive Example 2 was used. The encapsulation efficiency was calculated to be 95.1%.

Invention Example 29

Encapsulation Efficiency of Slurry of Semi-Permeable Particles of Invention Example 3 (Polycaprolactone and Glucose Oxidase)

The procedure of Invention Example 27 was followed except the W2 aqueous phase of an aqueous slurry of semi-permeable particles of the present invention as prepared in Invention Example 3 was used. The encapsulation efficiency was calculated to be 96.4%.

Invention Examples 27, 28, and 29 show that as the weight ratio of the water-insoluble semi-permeable polymer to organic catalytic material is increased, the encapsulation efficiency increased.

Invention Example 30

Retention Efficiency of a Slurry of Semi-Permeable Particles of Invention Example 4 (Polycaprolactone and Glucose Oxidase)

Retention efficiency is defined as the percentage of total organic catalytic material that is retained in the semi-permeable particles after storage under specified conditions for a given period of time.

To a clean cuvette were added 2.5 ml of a 0.008 weight % solution of o-dianisidine in 100 mmolar pH 6.0 phosphate buffer, 0.3 ml of an 18 weight % solution of glucose, and 0.1 ml of a 200 µg/ml solution of horseradish peroxidase. Upon temperature equilibration, 0.1 ml of the storage solution of an aqueous slurry of semi-permeable particles of the present invention as prepared in Invention Example 4 was added to the cuvette. The increase in absorbance was recorded at 460 nm over time. This increase in absorbance over time was compared to the increase in absorbance of the assay of the free organic catalytic material (described below in Comparative Example 6) to determine the amount of organic catalytic material in the storage solution. Since the amount of organic catalytic material is known in the free organic catalytic material assay, the amount of organic catalytic material is easily calculated in the storage solution.

| Storage Time (days) | Retention Efficiency |
| --- | --- |
| 1 | 100.0 |
| 18 | 100.0 |
| 70 | 100.0 |

These data show that the organic catalytic material was retained in semi-permeable particles of this invention over the time indicated.

Comparative Example 1

Assay of Slurry of Semi-Permeable Particles Derived from Polycaprolactone without Organic Catalytic Material The procedure of Invention Example 13 was followed except an aqueous slurry of semi-permeable particles outside of the present invention, as prepared in Invention Example 4 but omitting the glucose oxidase, was used.

| Time (minutes) | $A_{460\,nm}$ |
| --- | --- |
| 0 | 0.00 |
| 5 | 0.04 |
| 10 | 0.05 |
| 15 | 0.05 |

These data show that the semi-permeable particles outside of the present invention showed no catalytic activity. The absorbance did not change over time.

Comparative Example 2

Assay of Slurry of Semi-Permeable Particles Derived from Polycaprolactone without Organic Catalytic Material The procedure of Invention Example 23 was followed except an aqueous slurry of semi-permeable particles outside of this invention, as prepared in Invention Example 11 but omitting the catalase, was used.

| Time (minutes) | $A_{240\,nm}$ |
| --- | --- |
| 0 | 0.83 |
| 60.0 | 0.83 |
| 120.0 | 0.85 |

These data show that the slurry of semi-permeable particles outside of the present invention showed no catalytic activity. The absorbance did not change over time.

Comparative Example 3

Assay of Slurry of Semi-Permeable Particles Derived from Bisphenol Polyester without Organic Catalytic Material The procedure of Invention Example 24 was followed except an aqueous slurry of semi-permeable particles outside the present invention, as prepared in Invention Example 12 but omitting the catalase, was used.

| Time (minutes) | $A_{240\,nm}$ |
| --- | --- |
| 0 | 0.87 |
| 0.17 | 1.08 |
| 0.33 | 1.08 |
| 0.50 | 1.08 |
| 0.67 | 1.08 |
| 0.83 | 1.08 |
| 1.00 | 1.08 |
| 1.17 | 1.08 |
| 1.33 | 1.08 |
| 1.50 | 1.08 |

These data show that the slurry of semi-permeable particles outside the present invention showed no catalytic activity. The absorbance did not change over time.

Comparative Example 4

Assay of Slurry of Semi-Permeable Particles Derived from Polycaprolactone without Organic Catalytic Material The procedure of Invention Example 17 was followed except an aqueous slurry of semi-permeable particles outside the present invention, as prepared in Invention Example 5 but omitting the papain, was used.

| Time (minutes) | Volume NaOH (ml) |
| --- | --- |
| 40.00 | 0.05 |
| 78.33 | 0.10 |
| 106.67 | 0.15 |
| 151.67 | 0.20 |
| 195.83 | 0.25 |
| 242.58 | 0.30 |

These data show that the slurry of semi-permeable particles outside the present invention showed no catalytic activity Comparative Example 5

Assay of Slurry of Semi-Permeable Particles Derived from Bisphenol Polyester without Organic Catalytic Material The procedure of Invention Example 22 was followed except an aqueous slurry of semi-permeable particles outside the present invention, as prepared in Inventive Example 10 but omitting the papain, was used.

| Time (minutes) | Volume NaOH (ml) |
|---|---|
| 50.00 | 0.05 |
| 100.00 | 0.10 |
| 136.67 | 0.15 |
| 137.50 | 0.20 |
| 181.67 | 0.25 |
| 227.50 | 0.30 |

These data show that the slurry of semi-permeable particles outside the present invention showed no catalytic activity.

Comparative Example 6

Assay of Glucose Oxidase

To a clean cuvette were added 2.5 ml of a 0.008 weight % solution of o-dianisidine in 100 mmolar pH 6.0 phosphate buffer, 0.3 ml of an 18 weight % solution of glucose, and 0.1 ml of a 200 µg/ml solution of horseradish peroxidase. Upon temperature equilibration, 0.1 ml of a 1 µg/ml solution of glucose oxidase was added to the cuvette. The increase in absorbance was recorded at 460 nm over time. This increase in absorbance over time is proportional to the activity of glucose oxidase in units/mg of glucose oxidase.

| Time (minutes) | $A_{460\,nm}$ |
|---|---|
| 0.17 | 0.04 |
| 0.33 | 0.05 |
| 0.50 | 0.06 |
| 0.67 | 0.06 |
| 0.83 | 0.07 |
| 1.00 | 0.08 |
| 1.17 | 0.09 |
| 1.33 | 0.10 |
| 1.50 | 0.11 |
| 1.67 | 0.11 |
| 1.83 | 0.12 |
| 2.00 | 0.13 |

These data show that the free organic catalytic material showed catalytic activity. The activity of the glucose oxidase without the semi-permeable particles was calculated to be 130 U/mgP.

Comparative Example 7

Assay of Papain

To a clean vessel were added 4.0 ml of a 50 mmolar solution of L-cysteine in 20 mmolar ethylenediaminetetraacetic acid (pH was adjusted to 6.2 with 1 molar sodium hydroxide), 4.0 ml of a 3 molar sodium chloride solution, and 28 ml of an 80 mmolar solution of sodium benzoyl-L-arginine ethyl ester. The resulting solution was equilibrated to 25° C. in a water bath. Once equilibrated, 4.0 ml of a 1 U/ml solution of papain in deionized water were added. When the pH had fallen to 6.20, 50 µl of a 20 mmolar NaOH titrate solution was added. This was considered as time zero. When the pH again dropped to 6.20, an additional 50 µl of the 20 mmolar NaOH solution was added and the time was recorded. This procedure was repeated 5 to 6 times. The amount of titrate used over time is proportional to the papain activity in units/mg of papain (U/mgP).

| Time (minutes) | Volume NaOH (ml) |
|---|---|
| 1.17 | 0.05 |
| 1.67 | 0.10 |
| 2.23 | 0.15 |
| 2.73 | 0.20 |
| 3.32 | 0.25 |
| 3.80 | 0.30 |
| 4.28 | 0.35 |
| 4.78 | 0.40 |
| 5.25 | 0.45 |

These data show that the free organic catalytic material shows activity as the amount of NaOH needed to keep the pH at 6.2 increases over time. The activity of the papain without the semi-permeable particles was calculated to be 1.69 U/mgP.

Comparative Example 8

Assay of Horseradish Peroxidase

To a clean cuvette were added 1.4 ml of a solution of 0.0025 molar 4-aminoantipyrine and 0.17 molar phenol solution. To this was added 1.5 ml of a 0.0017 molar solution of hydrogen peroxide. Upon temperature equilibration, 0.1 ml of a 208 µg/ml solution of horseradish peroxidase was added. The increase in absorbance was recorded at 240 nm over time. The increase in absorbance over time is proportional to the activity of horseradish peroxidase in units/mg of horseradish peroxidase (U/mgP).

| Time (minutes) | $A_{510\,nm}$ |
|---|---|
| 0.37 | 0.00 |
| 0.54 | 0.01 |
| 0.70 | 0.02 |
| 0.87 | 0.03 |
| 1.04 | 0.04 |
| 1.20 | 0.06 |
| 1.37 | 0.08 |
| 1.54 | 0.10 |
| 1.70 | 0.12 |
| 1.87 | 0.14 |
| 2.04 | 0.17 |
| 2.20 | 0.19 |
| 2.37 | 0.21 |
| 2.54 | 0.23 |
| 2.70 | 0.26 |
| 2.87 | 0.28 |

These data show that the free organic catalyst shows catalytic activity. The activity of the horseradish peroxidase without the semi-permeable particles was calculated to be 247 U/mgP.

Comparative Example 9

Assay of Catalase

To a clean cuvette was added 1.9 ml of Reagent grade water and 1.0 ml of a 0.059 molar solution of hydrogen peroxide. Upon temperature equilibration, 0.1 ml of a 0.063 μg/ml solution of catalase was added. The decrease in absorbance was recorded at 240 nm over time and the change in absorbance over time was proportional to the activity of catalase in units/mg of catalase (U/mgP).

| Time (minutes) | $A_{240\,nm}$ |
| --- | --- |
| 0.19 | 0.71 |
| 0.37 | 0.68 |
| 0.54 | 0.67 |
| 0.70 | 0.65 |
| 0.87 | 0.64 |
| 1.04 | 0.62 |
| 1.20 | 0.61 |
| 1.37 | 0.60 |
| 1.54 | 0.58 |
| 1.70 | 0.57 |
| 1.87 | 0.56 |
| 2.04 | 0.55 |
| 2.20 | 0.54 |
| 2.37 | 0.54 |
| 2.54 | 0.53 |
| 2.70 | 0.52 |
| 2.87 | 0.51 |

These data show that the free organic catalytic material showed catalytic activity. The activity of the catalase without the semi-permeable particles was calculated to be 35,000 U/mgP.

The invention has been described in detail with particular reference to certain preferred embodiments thereof, but it will be understood that variations and modifications can be effected within the spirit and scope of the invention.

The invention claimed is:

1. An aqueous slurry of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle has a mode particle size of at least 1 μm,
wherein each semi-permeable particle is impermeable to the organic catalytic material, and the semi-permeable particle is permeable to molecules having a molar mass that is 1000 Daltons or less, and
the organic catalytic material is selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase,
wherein each semi-permeable particle further comprises an amphiphilic block copolymer that is disposed at the interface of the multiple discrete cavities and the continuous polymeric phase, which amphiphilic block copolymer has an HLB value of less than or equal to 6.

2. The aqueous slurry of semi-permeable particles of claim 1, wherein the water-insoluble semi-permeable polymer and the aqueous solution or suspension of the organic catalytic material are present in each semi-permeable particle at a weight ratio of at least 0.04 to and including 3.5.

3. The aqueous slurry of semi-permeable particles of claim 1, wherein the water-insoluble semi-permeable polymer is selected from a polyester, polyamide, polyurethane, styrenic polymer, mono-olefin polymer, vinyl ester polymer, acrylic polymer, vinyl ether polymer, vinyl ketone polymer, and aliphatic cellulose ester polymer.

4. The aqueous slurry of semi-permeable particles of claim 1, wherein the cavity stabilizing hydrocolloid is selected from the group consisting of carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropane-sulfonate), and a polyphosphate.

5. The aqueous slurry of semi-permeable particles of claim 1, wherein each semi-permeable particle has a mode particle size of at least 1 μm and up to and including 100 μm.

6. The aqueous slurry of semi-permeable particles of claim 1, wherein the volume of the multiple discrete cavities in each semi-permeable particle is at least 10% and up to and including 60% of the total semi-permeable particle volume.

7. The aqueous slurry of semi-permeable particles of claim 1, wherein the average discrete cavity size is at least 200 nm to and including 5 μm.

8. The aqueous slurry of semi-permeable particles of claim 1 wherein each semi-permeable particle further comprises a surface stabilizing material on the external particle surface.

9. The aqueous slurry of semi-permeable particles of claim 1, wherein each semi-permeable particle further comprises colloidal or fumed silica on the external particle surface.

10. The aqueous slurry of semi-permeable particles of claim 1, wherein each semi-permeable particle has a mode particle size of at least 2 μm and up to and including 40 μm.

11. The aqueous slurry of semi-permeable particles of claim 1, wherein at least 80% of the organic catalytic material is actively retained in the semi-permeable particles after storage for more than 30 days at room temperature as an aqueous slurry.

12. The aqueous slurry of semi-permeable particles of claim 1, wherein the amphiphilic block copolymer comprises: a hydrophilic segment that comprises a polyamide, polycarbonate, polyethylene oxide, poly(2-ethoxazoline), poly(saccharide) or dextran; and an oleophilic segment that comprises a poly(caprolactone), poly(lactic acid), poly(3-hydroxybutyrate-co-3-hydroxyvalerate), poly(3-hydroxybutyrate), or poly(glycolic acid).

13. The aqueous slurry of semi-permeable particles of claim 1, wherein the amphiphilic block copolymer is present in the semi-permeable particles in amount of at least 1 weight % and up to and including 99.5 weight %, based on the total semi-permeable particle weight.

14. The aqueous slurry of semi-permeable particles of claim 1, wherein the amphiphilic block copolymer comprises a poly(caprolactone) oleophilic segment and a polyethyleneoxide hydrophilic segment.

15. A material useful for catalyzing chemical reactions in substantially aqueous media, the material comprising an aqueous slurry of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, each semi-permeable particle having a mode particle size of at least 1 µm, wherein each semi-permeable particle is impermeable to the organic catalytic material, and each semi-permeable particle is permeable to molecules having a molar mass that is 1000 Daltons or less, and the organic catalytic material is selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrite hydrolas, wherein each semi-permeable particle further comprises an amphiphilic block copolymer that is disposed at the interface of the multiple discrete cavities and the continuous polymeric phase, which amphiphilic block copolymer has an HLB value of less than or equal to 6.

16. A method of making an aqueous slurry of a plurality of semi-permeable particles, each semi-permeable particle comprising a water-insoluble, semi-permeable polymer providing a continuous polymeric phase including an external particle surface, each semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle having a mode particle size of at least 1 µm, wherein each semi-permeable particle is impermeable to the organic catalytic material, and each semi-permeable particle is permeable to molecules having a molar mass that is 1000 Daltons or less, the method comprising:

providing a first aqueous phase comprising the organic catalytic material and the cavity stabilizing hydrocolloid, both dispersed within the first aqueous phase, dispersing the first aqueous phase in an oil phase comprising an organic solvent comprising the water-insoluble semi-permeable polymer to form a first water-in-oil emulsion, the oil phase further comprising an amphiphilic block copolymer, which amphiphilic block cuolvmer has an HLB value of less than or equal to 6, dispersing the first water-in-oil emulsion in a second aqueous phase containing a surface stabilizing material to form a water-in-oil-in-water emulsion containing droplets of the water-in-oil emulsion, and removing the organic solvent from the droplets to form the aqueous dispersion of a plurality of semi-permeable particles, and wherein the organic catalytic material is selected from the group consisting of catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase, wherein each semi-permeable particle further comprises the amphiphilic block copolymer that is disposed at the interface of the multiple discrete cavities and the continuous polymeric phase, which amphiphilic block copolymer has an HLB value of less than or equal to 6.

17. The method of claim 16, wherein the water-insoluble semi-permeable polymer in the semi-permeable particles is selected from a polyester, polyamide, polyurethane, styrenic polymer, mono-olefin polymer, vinyl ester polymer, acrylic polymer, vinyl ether polymer, vinyl ketone polymer, and aliphatic cellulose ester polymer.

18. The method of claim 16, wherein the cavity stabilizing hydrocolloid is selected from the group consisting of carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropanesulfonate), and a polyphosphate.

19. The method of claim 16, wherein each of the plurality of semi-permeable particles further comprises a surface stabilizing material on the external particle surface.

20. The method of claim 16, wherein the water-insoluble semi-permeable polymer and aqueous solution or suspension of the organic catalytic material are present at a weight ratio of at least 0.04 to and including 3.5.

21. The method of claim 16, wherein the amphiphilic block copolymer comprises a polycaprolactone oleophilic segment.

22. The method of claim 16, wherein the oil phase further comprises the amphiphilic block copolymer in an amount of at least 0.2 weight % and up to and including 30 weight %, based on the total oil phase weight.

23. A method for causing a chemical reaction, comprising:
contacting one or more reactive chemicals having a molar mass of 1000 Daltons or less with a slurry of semi-permeable particles, each of the semi-permeable particles comprising a water-insoluble semi-permeable polymer providing a continuous polymeric phase including an external particle surface, the semi-permeable particle further comprising multiple discrete cavities within the continuous polymeric phase, and having disposed within at least some of the multiple discrete cavities: (a) a cavity stabilizing hydrocolloid, and (b) an aqueous solution or suspension of an organic catalytic material, and each semi-permeable particle has a mode particle size of at least 1 µm, wherein each semi-permeable particle is impermeable to the organic catalytic material, and the semi-permeable particle is permeable to molecules of the reactive chemical having a molar mass of 1000 Daltons or less, wherein each semi-permeable particle further comprises the amphiphilic block copolymer that is disposed at the interface of the multiple discrete cavities and the continuous polymeric phase, which amphiphilic block copolymer has an HLB value of less than or equal to 6.

24. The method of claim 23, after chemical reaction of the organic catalytic material with the reactive chemical, the slurry of semi-permeable particles is reused by contacting the semi-permeable particles with the same or different chemical reactant.

25. The method of claim 23, wherein the water-insoluble semi-permeable polymer and the aqueous solution or suspension of the organic catalytic material are present in each semi-permeable particle at a weight ratio of at least 0.04 to and including 3.5.

26. The method of claim 23, wherein the cavity stabilizing hydrocolloid is selected from the group consisting of carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropanesulfonate), and a polyphosphate.

27. The method of claim 23, wherein the volume of the multiple discrete cavities in each semi-permeable particle is at least 10% and up to and including 60% of the total semi-permeable particle volume.

28. The method of claim 23, wherein the average discrete cavity size in each semi-permeable particle is at least 200 nm to and including 5 μm.

29. The method of claim 23, wherein each semi-permeable particle has a mode particle size of at least 2 μm and up to and including 40 μm.

30. The method of claim 23, wherein the amphiphilic block copolymer comprises: a hydrophilic segment that comprises a polyamide, polycarbonate, polyethylene oxide, poly(2-ethoxazoline), poly(saccharide) or dextran; and an oleophilic segment that comprises a poly(caprolactone), poly(lactic acid), poly(3-hydroxybutyrate-co-3-hydroxyvalerate), poly(3-hydroxybutyrate), or poly(glycolic acid).

\* \* \* \* \*